United States Patent [19]
Saiya et al.

[11] 4,149,610
[45] Apr. 17, 1979

[54] ACOUSTIC HEADSETS

[75] Inventors: Robert F. Saiya, N. Babylon; Gerald J. Gottlieb, Huntington; Samuel J. Kravis, Babylon, all of N.Y.

[73] Assignee: Instrument Systems Corporation, Huntington, N.Y.

[21] Appl. No.: 722,314

[22] Filed: Sep. 10, 1976

[51] Int. Cl.² .............................................. A61B 7/02
[52] U.S. Cl. .................................... 181/131; 181/135
[58] Field of Search ...................... 181/131, 135, 137; 179/1 ST, 182 A, 156 R

[56] References Cited
U.S. PATENT DOCUMENTS

| 882,700 | 3/1908 | Lewis | 181/131 |
|---|---|---|---|
| 1,245,217 | 11/1917 | Gottschalk | 181/131 |
| 3,623,571 | 11/1971 | French | 181/135 |
| 3,730,290 | 5/1973 | Scanlon | 181/135 |
| 3,772,478 | 11/1973 | McCabe et al. | 179/1 ST |
| 3,776,362 | 12/1973 | Rice | 181/135 |
| 3,934,674 | 1/1976 | Shore et al. | 181/131 |
| 4,011,925 | 3/1977 | French et al. | 181/131 |

Primary Examiner—Stephen J. Tomsky
Attorney, Agent, or Firm—Blum, Moscovitz, Friedman & Kaplan

[57] ABSTRACT

An acoustic headset having a pair of elongated channel structures for carrying sound tubes which are provided with ear pieces situated adjacent upper end regions of the channel structures. These channel structures have distant from their upper end regions, respectively, lower end regions interconnected with each other by way of a connecting structure which forms a continuous, elongated, one-piece body with the pair of channel structures. The connecting structure interconnects the pair of channel structures for movement toward and away from each other while a releasable holding structure is connected with the pair of channel structures for releasably holding them at a selected distance from each other, so that in this way it is possible for the ear pieces to be accommodated to the distance between the ears of a given individual.

11 Claims, 19 Drawing Figures

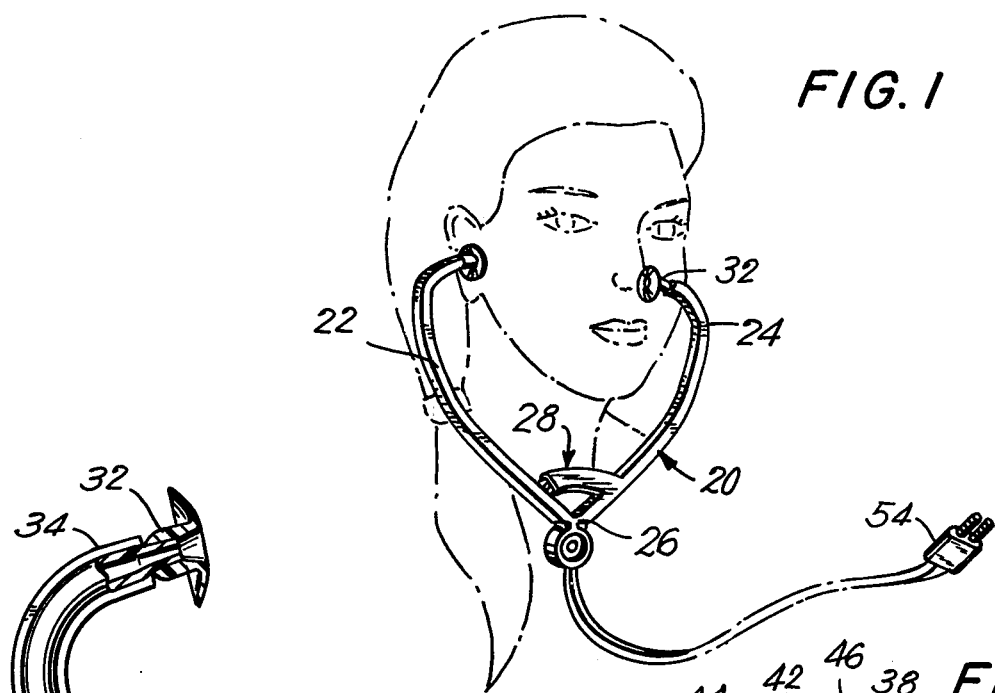
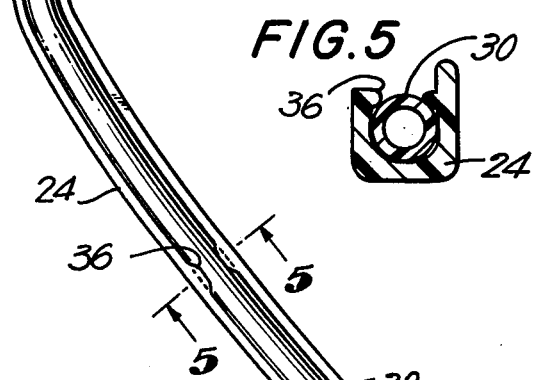
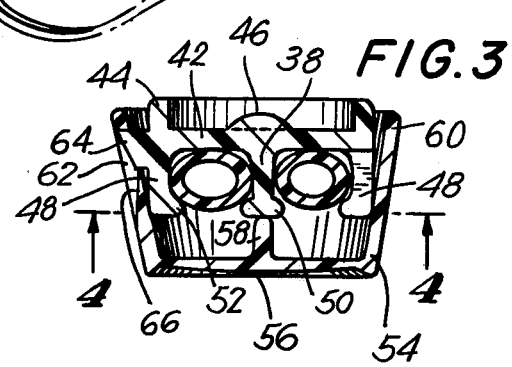
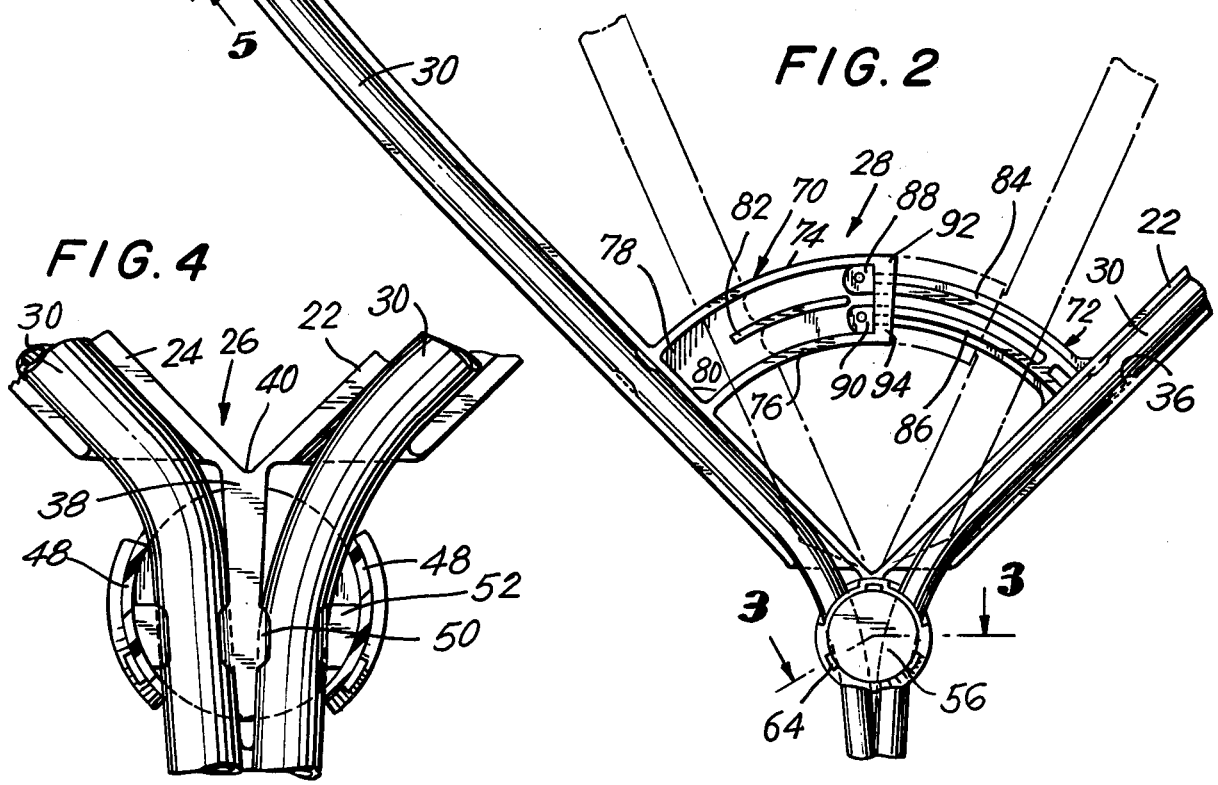
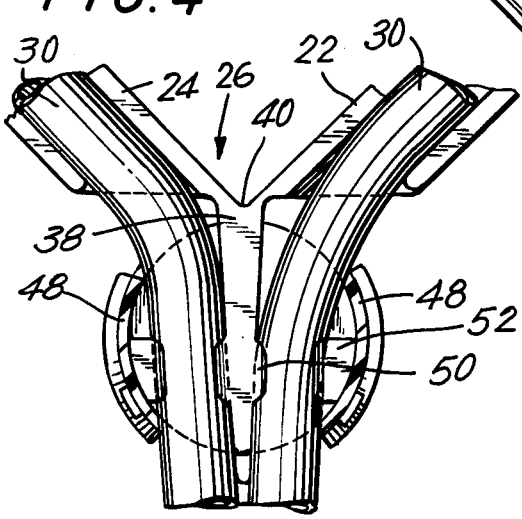

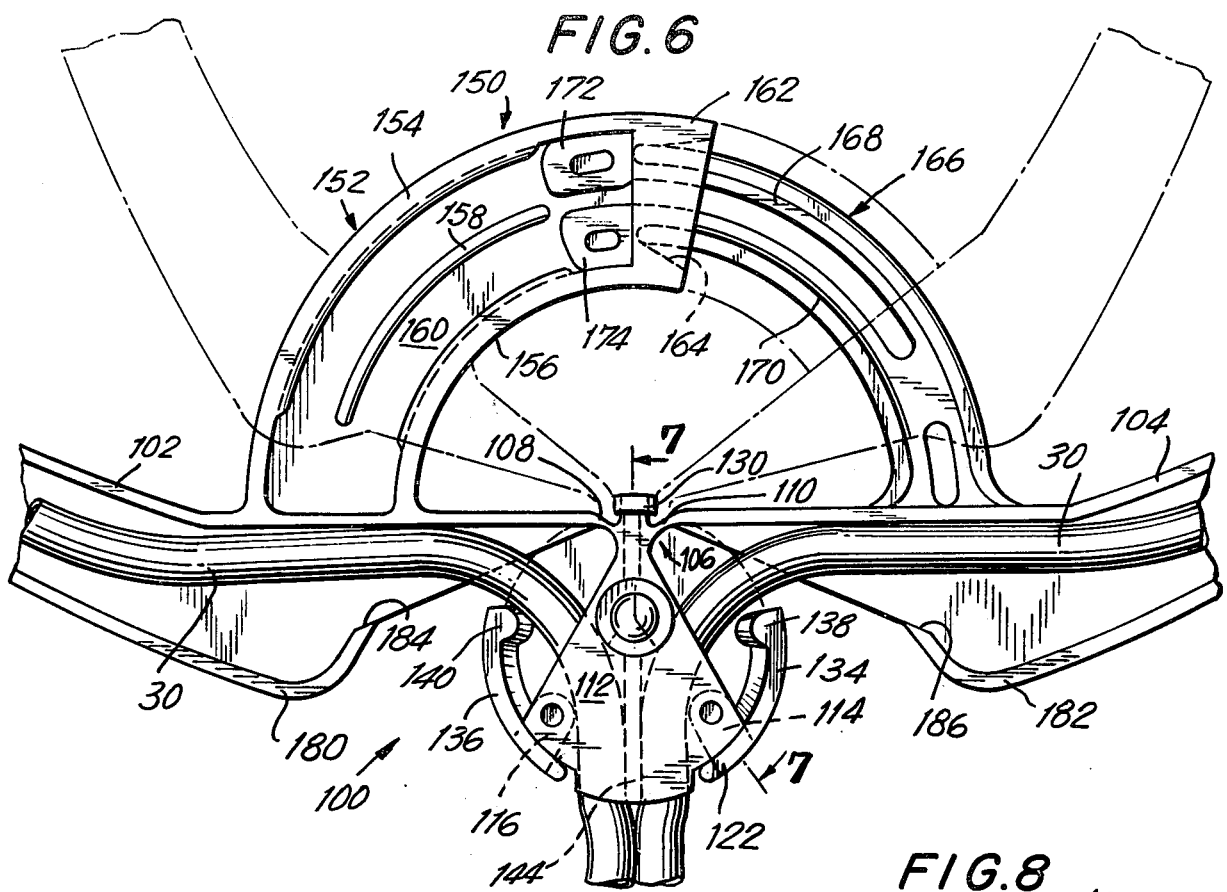
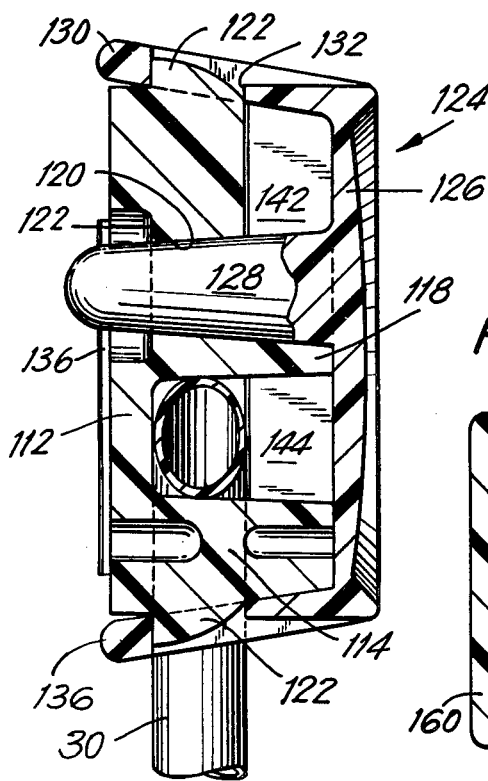
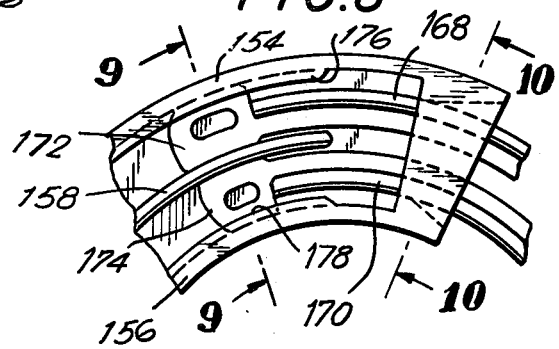
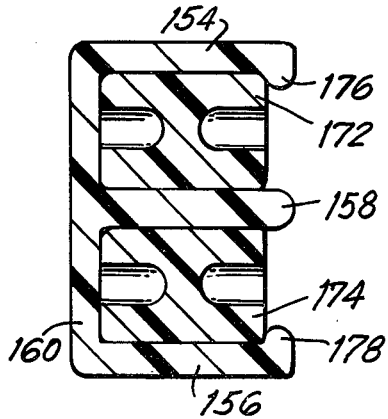
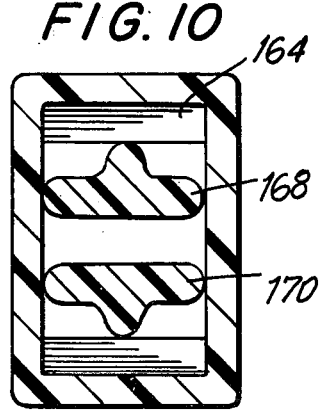

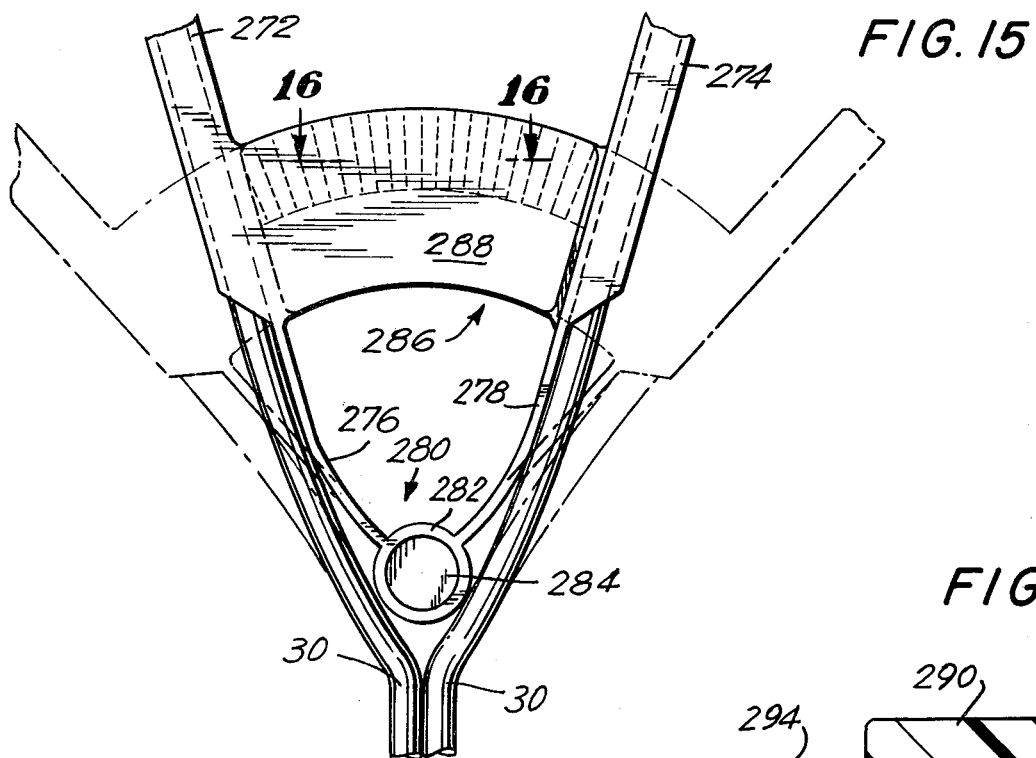
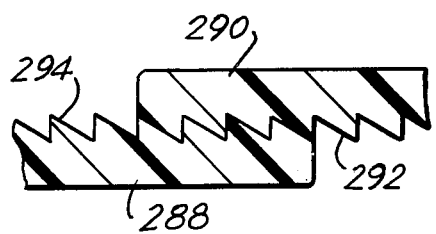
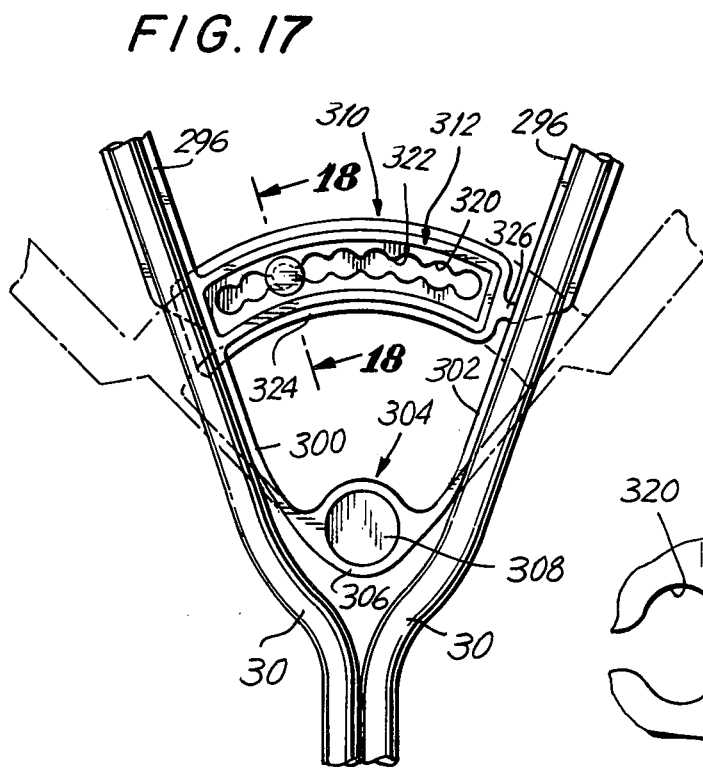
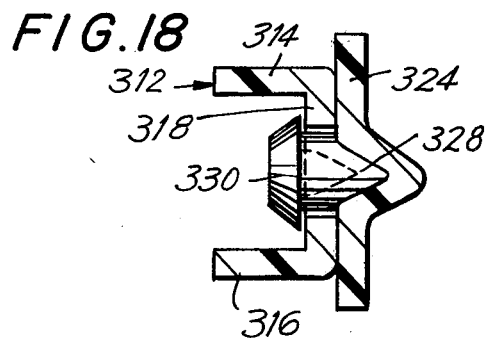
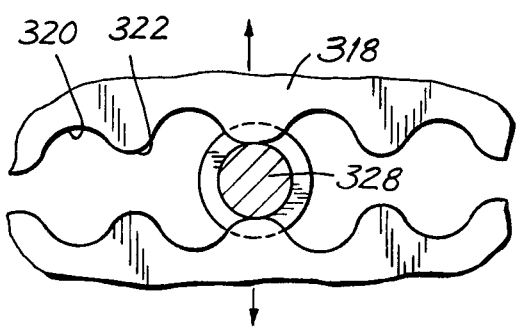

ACOUSTIC HEADSETS

BACKGROUND OF THE INVENTION

The present invention relates to acoustic headsets.

The present invention relates in particular to acoustic headsets of the stethoscope type as used, for example, on airplanes for the purpose of enabling travelers to listen to sounds emanating from recordings, movie sound tracks, or the like.

Acoustic headsets of the above type are of course well known. However, these known headsets suffer from serious drawbacks. Thus, with certain types of stethoscope headsets it is conventional to interconnect the elongated opposed arms of the headset with a springy structure which urges these arms toward each other so that when the headset is not used the ear pieces thereof are situated quite close to each other. The individual using such a headset spreads the arms thereof apart from each other in order to place the ear pieces at a distance from each other required to mount the ear pieces at the ears of the individual. Such headsets are of course designed so that relatively small individuals such as children, who require the ear pieces to be situated at a relatively small distance from each other, can use the same headset as an adult with even a relatively large distance between the ears. The result is that for most individuals the ear pieces press against the ears in an undesirable manner, particularly in view of the fact that headsets in airplanes are used for relatively long intervals.

Although there are also known headsets of the above general type which include an adjustable structure by means of which it is possible to adjustably hold the arms at a given distance from each other, these structures are relatively complex and difficult to manipulate, while at the same time being undesirably expensive and adjustable only with considerable inconvenience.

SUMMARY OF THE INVENTION

It is accordingly a primary object of the present invention to provide an acoustic headset which will avoid the above drawbacks.

In particular, it is an object of the present invention to provide an acoustic headset which when used will not require the ear pieces to be urged toward each other with a force which will render the headset uncomfortable to wear over a long interval.

In particular, it is an object of the present invention to provide a headset of the above general type which can have the ear pieces thereof quickly and conveniently situated at a desired distance from each other, with the ear pieces remaining reliably at this desired distance without pressing undesirably against the ears of the individual using the headset.

It is also an object of the present invention to provide a structure of this type which is extremely simple and inexpensive while at the same time being convenient to operate.

It is also an object of the present invention to provide a construction of the above general type which while being simple and inexpensive nevertheless has a long trouble-free operating life, while at the same time being of an attractive appearance and having a light weight.

According to the invention, the acoustic headset includes a pair of elongated channel means for carrying a pair of sound tubes which are respectively provided with ear pieces situated respectively adjacent upper end regions of the pair of channel means. This pair of channel means respectively have lower end regions distant from their upper end regions, and a connecting means interconnects the pair of channel means at their lower end regions for providing for movement of the pair of channel means toward and away from each other, this connecting means forming with the pair of channel means an elongated continuous one-piece body. A releasable holding means is operatively connected with the pair of channel means for releasably holding the latter at a selected distance from each other according to which it is possible to accommodate the distance between the ear pieces to the distance between the ears of a given individual.

BRIEF DESCRIPTION OF DRAWINGS

The invention is illustrated by way of example in the accompanying drawings which form part of this application and in which:

FIG. 1 shows in elevation one possible embodiment of an acoustic headset according to the invention, the headset being shown in FIG. 1 during use thereof by an individual represented in phantom lines;

FIG. 2 is a fragmentary partly sectional elevation of the acoustic headset of FIG. 1 as it appears when looking toward the rear of the headset, FIG. 2 showing in phantom lines how the pair of channel means can be displaced from the positions thereof shown in solid lines in FIG. 2;

FIG. 3 is a sectional plan view of part of the structure of FIG. 2 taken along line 3—3 of FIG. 2 in the direction of the arrows and showing the structure at a scale which is enlarged as compared to FIG. 2;

FIG. 4 is a sectional elevation, taken along line 4—4 of FIG. 3 in the direction of the arrows, and fragmentarily showing the details of a connecting means for interconnecting the pair of channel means of the headset of FIGS. 1 and 2;

FIG. 5 is a transverse section of a channel means and a sound tube therein, FIG. 5 being taken along line 5—5 of FIG. 2 in the direction of the arrows;

FIG. 6 is a fragmentary elevation illustrating the lower end regions of a pair of elongated channel means of another embodiment of a headset according to the invention, FIG. 6 showing the details of the connecting means which interconnects the pair of channel means and a releasable holding means cooperating with the pair of channel means, and FIG. 6 also showing in phantom lines positions of the pair of channel means different from those shown in solid lines in FIG. 6;

FIG. 7 is a sectional elevation of the connecting means of FIG. 6 taken along line 7—7 of FIG. 6 in the direction of the arrows and showing the structure at a scale which is enlarged as compared to FIG. 6;

FIG. 8 is a fragmentary illustration of part of the releasable holding means of FIG. 6 shown in a position different from that illustrated in FIG. 6;

FIG. 9 is a transverse section of the structure of FIG. 8 taken along line 9—9 of FIG. 8 in the direction of the arrows;

FIG. 10 is a transverse section of the structure of FIG. 8 taken along line 10—10 of FIG. 8 in the direction of the arrows;

FIG. 15 is a fragmentary front elevation of yet another embodiment of the invention showing only the lower end regions of the pair of channel means while illustrating the connecting means and releasable holding means, with FIG. 15 also showing in phantom lines a position of adjustment different from that illustrated in solid lines;

FIG. 16 is a fragmentary sectional plan view taken along line 16—16 of FIG. 15 for further illustrating details of the releasable holding means of the embodiment of FIG. 15;

FIG. 17 is a fragmentary rear elevation of yet another embodiment of an acoustic headset according to the invention, with FIG. 17 also showing only the lower end regions of the pair of channel means while showing in detail the structure of the connecting means which interconnects the pair of channel means and the details of the releasable holding means used in this embodiment;

FIG. 18 is a transverse section of the releasable holding means of FIG. 17 taken along line 18—18 of FIG. 17 in the direction of the arrows and showing the structure at a scale which is enlarged as compared to FIG. 17; and FIG. 19 is a fragmentary schematic elevation, partly in section, illustrating how the releasable holding means of FIGS. 17 and 18 operates.

DESCRIPTION OF PREFERRED EMBODIMENTS

Figure 11:
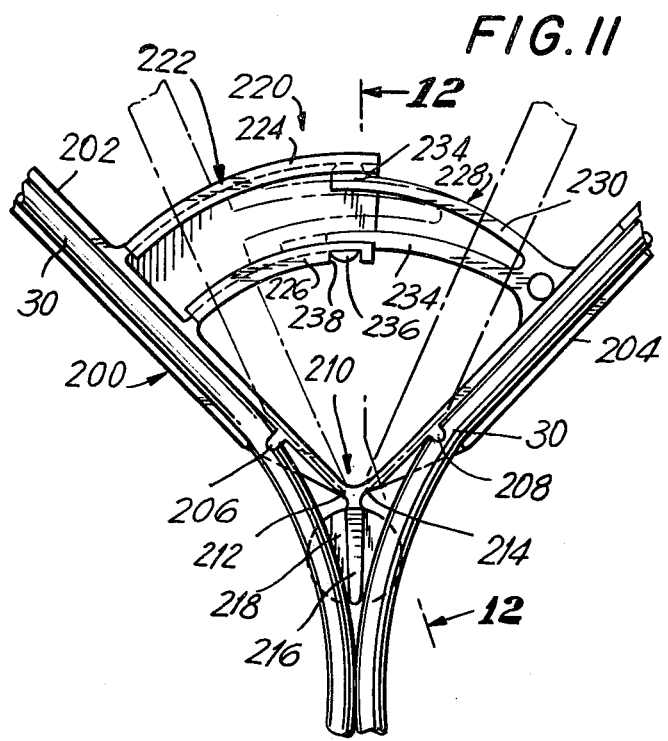
FIG. 11 is a fragmentary elevation also showing only the lower end regions of a pair of channel means with FIG. 11 showing the structure, in the same way as in FIGS. 2 and 6, as it appears when looking toward the rear of the structure, with FIG. 11 showing the details of the connecting means and releasable holding means of this embodiment which is different from the embodiments of FIGS. 2 and 6, and FIG. 11 also illustrating in phantom lines an adjusted position different from that shown in solid lines.

Referring to FIG. 1, the acoustic headset 20 illustrated therein includes a pair of elongated channel means 22 and 24 interconnected by way of a connecting means 26 which serves to connect the pair of channel means 22 and 24 for movement toward and away from each other. In order to hold the pair of channel means 22 and 24 at a selected distance from each other, a releasable holding means 28 is operatively connected with the pair of channel means 22 and 24.

The details of the headset 20 of FIG. 1 are illustrated in FIG. 2 which shows the headset 20 as it appears when looking toward the rear thereof, while FIG. 1 illustrates the headset as it appears when looking toward the front thereof. Thus, referring to FIG. 2, it will be seen that the elongated channel means 24 is in the form of an elongated channel member having the illustrated configuration for carrying an elongated sound tube 30 which at its upper end carries an ear piece 32 situated adjacent the upper end region 34 of the channel means 24. The channel means 24 is provided at the edge regions of its opposed side walls at suitably spaced locations with inwardly directed projections 36 which serve to hold the sound tube 30 within the channel means 24, in the manner most clearly apparent from FIGS. 2 and 5. It will be understood that the channel means 22 is identical with the channel means 24, being a mirror image thereof, with the channel means 22 also being provided with pairs of projections 36 suitably spaced therealong for retaining a second sound tube 30 within the channel means 22. Of course this sound tube 30 carried by the channel means 22 also is provided at its upper end with a second ear piece identical with the ear piece 32.

As is apparent from FIG. 4, the connecting means 26 is integral with the pair of channel means 22 and 24 at the lower end regions of the latter, the connecting means 26 as well as the channels 22 and 24 being made of a suitable plastic material and all being integral with each other so that the pair of channel means 22 and 24 together with the connecting means 26 form an elongated continuous one-piece structure. The connecting means 26 includes an elongated substantially vertically extending member 38 forming a hinged connection 40 with the pair of channel means 22 and 24. This hinge 40 is a plastic hinge of known construction providing for the pair of channel means 22 and 24 completely free turning movement with respect to each other about the axis defined by the hinge 40 and with substantially no resistance to swinging movement of the pair of channel means 22 and 24 one with respect to the other.

Beneath the hinge 40 the arm 38 of the connecting means is integrally formed with a front circular member or wall 42 integral with a forwardly extending circular lip 44 and having a central boss 46 so that when looking toward the connecting means 26 at the front thereof, as shown in FIG. 1, the connecting means has an attractive appearance. The wall 42 is integral with the pair of rearwardly extending arcuate wall portions 48 which are respectively situated on opposite sides of the wall 38 while being spaced therefrom so that the pair of sound tubes can be accommodated between the wall 38 and each of the walls 48. As is apparent from FIG. 3, each wall 48 may be interrupted at a given location, as shown for the right wall 48 of FIG. 3, so as to facilitate introduction of the sound tubes between the walls 48 and respectively on opposite sides of the wall 38. In order to hold the tubes 30 in position the wall 38 has a pair of opposed projections 50 while the walls 48 are respectively provided with inwardly extending projections 52. Thus the pair of sound tubes 30 are held in a forward and rearward direction between the front wall 42 and the rear projections 50 and 52 while being held in a right and left direction between the outer walls 48 and the intermediate wall 38. The sound tubes 30 extend to a known plug structure 54 (FIG. 1), by means of which the sound tubes 30 are interconnected with the source of the sound which is to be listened to by the individual using the headset 20.

The connecting means 26 is completed by a cap means 54 having a rear end wall 56 integral with a forwardly extending projection 58 which engages the rear surface of the wall 38 in the manner shown in FIG. 3. This cap means 54 has a tapered side wall 60 formed with openings 62 for receiving projections 64 situated at the periphery of the wall 42, and being integral therewith while projecting therefrom. These projections 64 are suitably spaced around the periphery of the wall 42, as shown most clearly in FIG. 2, and the cap 50 is simply pressed onto the wall 42 with the projections 64 snapping into the openings 62 while the cap 54 has tongues 66 which engage the projections 64 in the manner shown at the left of FIG. 3 for also limiting the movement of the cap means onto the central portion of the connecting means 26. Thus, by way of the cap means 54 the headset is provided with a smooth rear surface to be directed toward the body of the individual using the headset, while at the same time at the front of the headset there is also a smooth-surfaced appearance, as is apparent from FIG. 1.

With the structure as described above the pair of channel means 22 and 24 can simply be turned with practically no resistance at the axis formed by the hinge 40 of the connecting means 26, so that it is a simple matter for the operator to situate the ear pieces at the desired distance from each other. In order to releasably hold the ear pieces at a selected distance from each other, the releasable holding means 28 is provided. This releasably holding means 28 includes a pair of components 70 and 72 integrally formed with the pair of channel means 24 and 22 projecting therefrom toward each other, as shown most clearly in FIG. 2. The component 70 has a pair of concentric arcuate side wall portions 74 and 76 defining between themselves a hollow interior space 78 for receiving the component 72. The side walls 74 and 76 are interconnected by an integral front wall 80 so that the component 70 is in fact in the form of a curved channel member. Between the side walls 74 and 76 the component 70 has an intermediate arcuate wall 82 integral with and projecting from the front wall 80 and situated midway between while being concentric with the arcuate walls 74 and 76. Thus, the intermediate wall 82 is situated in the hollow interior 78 of the component 70.

The component 72 is formed integrally with the channel means 22, being made of the same material as the channel means 22, while the component 70 is also integral with the channel means 24 and made of the same material as the channel means 24, so that both of the channel means 22 and 24 together with the connecting means 26, except for the cap means 54 thereof, and the pair of components 70 and 72 of the releasable holding means 28 can all be integrally molded in one piece of a suitable plastic material forming in this way only a one-piece structure for the entire headset, except for the cap means 54, and of course except for the sound tubes 30 and the ear pieces 32 carried thereby. The component 72 includes a pair of springy fingers 84 and 86 which are also of an arcuate configuration and which are concentric with each other while having, for example, an angled cross section. The springy fingers 84 and 86 are spaced from each other and respectively terminate in a pair of enlarged free end portions 88 and 90, respectively. At their right free ends, as viewed in FIG. 2, the walls 74 and 76 as well as the wall 80 are interconnected by a transverse end wall 92 formed with a tapered opening 94. The end portion 88 and 90 of the springy fingers 84 and 86 can be slipped through the tapered opening 94 into the hollow interior of the component 70. After passing through the opening 94, the springy fingers 84 and 86 spread apart from each other and the end portions 88 and 90 form shoulders directed toward the right, as viewed in FIG. 2, and engaging the inner surface of the transverse end wall 92, so that in this way the end wall 92 forms a means which limits the outward movement of the component 72 from the interior 78 of the component 70.

The pair of channel means 22 and 24 are shown in solid lines in FIG. 2 at their furthest distance from each other where the end portions 88 and 90 of the fingers 84 and 86 engage the transverse wall 92. From this extreme position it is possible for the operator to turn the pair of channel means 22 and 24 toward each other, for example to the phantom line position shown in FIG. 2. This movement will result in situating the end portion 88 of finger 84 between the wall 74 and the intermediate wall 82, while at the same time the end portion 90 of the finger 86 will become situated between the wall 76 and the intermediate wall 82. The size of the end portions 88 and 90 is such that these end portions will frictionally rub against the intermediate wall 82 as well as against the inner surfaces of the side wall 74 and 76, and this friction is great enough to hold the pair of channel means 24 and 22 at a selected distance from each other. The frictional resistance to turning of the pair of channel means 22 and 24 with respect to each other can be relatively small while at the same time the releasable holding means 28 will reliably hold the pair of channel means at a selected position with respect to each other because of the extremely small, practically negligible resistance to turning provided by way of the hinge 40.

Thus, with the above structure of FIGS. 1-5 a simple plastic headset is provided which can readily be adjusted by the operator without the necessity of overcoming a substantial spring force while at the same time the adjusted position of the pair of channel means 22 and 24 will be reliably maintained due to the frictional cooperation between the components 72 and 70 of the releasable holding means 28.

Referring now to the embodiment of the invention which is illustrated in FIGS. 6-10, the headset 100 illustrated therein includes a pair of elongated channel means 102 and 104 of which only the lower end regions are illustrated in FIG. 6. The pair of channel means 102 and 104 at their unillustrated portions are identical with the pair of channel means described above and in the same way accommodate sound tubes 30 which at the unillustrated upper end regions of the pair of channel means 102 and 104 carry a pair of ear pieces in the same way as the embodiment of FIGS. 1-5. The structure is shown in FIG. 6 at it appears when looking toward the rear thereof.

The pair of elongated channel means 102 and 104 are integral with a connecting means 106 which forms a pair of freely turnable hinge connections 108 and 110 with the pair of channel means 102 and 104. This connecting means 106 includes a wall 112 of substantially triangular configuration, as shown most clearly in FIG. 6. At its upper substantially pointed region the wall 112 is integrally formed with the hinges 108 and 110 which provide for the free turning of the pair of channel means 102 and 104 with respect to each other. A pair of projections 114 and 116 are integral with and project forwardly from the wall 112, this wall 112 also having a substantially central projection 118 and being formed just above the latter with a tapered bore 120 terminating in a rear recess 122 of the wall 112, the upper surface of the projection 118 conforming to the taper of the bore 120. Thus the projection 118 has an upper concave tapered surface and a lower convex surface. The upper ends of the forward projections 114 and 116 are convexly curved, as is apparent from FIG. 6, and these upper ends of the projections 114 and 116 form with the lower convex surface of the projection 118 channels through which the pair of sound tubes 30 extend in the manner apparent from FIGS. 6 and 7. At its upper end as well as at the lower ends of the projections 114 and 116 the member 112 is formed with curved teeth 122, for a purpose referred to below.

The wall 112 carries a cap means 124 which has a circular front wall 126 behind which the wall 112 is situated. This front wall 126 carries a tapered pin 128 which is received in the tapered bore 120 in the manner apparent from FIG. 7. In addition the cap means 124 is provided at its upper part with a rearwardly extending tongue 130 formed with an opening 132 for receiving the upper tooth 122 in the manner apparent from FIG. 7. The front wall 126 also is provided with an integral pair of rearwardly extending arcuate portions 134 and 136 respectively formed with openings for receiving the pair of lower teeth 122 which project from the portions 114 and 116. The arcuate portions 134 and 136 are respectively provided at their upper ends with curved bosses 138 and 140 which guide the tubes 30 into the space between the projections 114 and 116, beneath the projection 118 as is apparent from FIGS. 6 and 7. The wall 126 has integrally formed therewith a pair of diametrically extending ribs 142 and 144, the upper rib 142 projecting upwardly from the pin 128 and engaging the front surface of the wall 112 above the bore 120 while the lower rib 144 extends beneath the projection 118 straight down from the latter to define with the pair of projections 114 and 116 a pair of passages through which the tubes 30 respectively extend as is apparent from FIGS. 6 and 7.

Thus, with the above structure it is easily possible for the operator to turn the pair of channel means 102 and 104 to any desired angular position with respect to each other.

The pair of channel means 102 and 104 capable of being releasably held in a selected position with respect to each other by a releasable holding means 150 which is substantially identical with the releasable holding means 28 of FIGS. 1-5. This releasable holding means 150 includes an arcuate channel component 152 which is integral with and projects from the channel means 102 and which has opposed concentric side walls 154 and 156 as well as an intermediate wall 158 projecting from the front wall 160 which is integral with the walls 154, 156, and 158. The walls 154, 156, and 160 are integral with an end wall 162 formed with a tapered opening 164 through which the springy fingers of the component 166 of the releasable holding means 150 can pass. These springy fingers 168 and 170 are integrally connected with the channel means 104 in the manner apparent from FIG. 6. Each of these fingers is of a substantially T-shaped cross section, as is apparent from FIG. 10. The springy fingers 168 and 170 terminate in the enlarged free end portions 172 and 174 which form shoulders for engaging the inner surface of the transverse wall 162 once these portions 172 and 174 pass through the opening 164, so that this embodiment also has the means which prevents removal of the component 166 from the interior of the component 150. When the pair of channel means are displaced toward each other from the solid line position shown in FIG. 6 to the dot-dash line position, for example, the free end portions 172 and 174 respectively slide along the inner surfaces of the walls 154 and 156 as well as the opposed surfaces of the intermediate wall 158, in the manner which is most clearly apparent from FIGS. 8 and 9. Thus due to this frictional engagement of the component 166 with the component 150 in the interior of the latter it is possible for the operator to releasably retain the pair of channel means 102 and 104 in a selected position with respect to each other. As is apparent from FIGS. 8 and 9, the walls 154 and 156 are formed with inwardly directed lips 178 which extend in part over the projections 172 and 174 so as to reliably retain the latter in the hollow interior of the component 152.

Of course the releasable holding means 150 of FIGS. 6 and 8-10 can also be utilized in all of its details for the embodiment of FIGS. 1-5.

The pair of channel means 102 and 104 are provided with outer walls 180 and 182, respectively, which terminate in the end edges 184 and 186, so that beyond these end edges there are free spaces through which the tubes 30 can freely pass in the manner apparent from FIG. 6.

Figure 12:
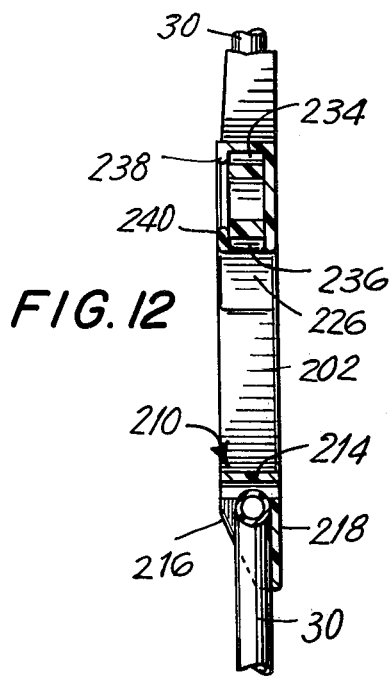
FIG. 12 is a sectional elevation of the structure of FIG. 11 taken along line 12—12 of FIG. 11 in the direction of the arrows.

In the embodiment of the invention which is illustrated in FIGS. 11 and 12, the headset 200 has a pair of channel means 202 and 204, only the lower ends of which are illustrated in FIG. 11. The portions beyond these lower end regions are identical with those of the above-described embodiments and in the same way carry the pair of sound tubes 30 which are of course connected at their upper ends with ear pieces situated adjacent the unillustrated upper end regions of the pair of channel means 202 and 204. At their lower end regions the pair of channel means 202 and 204 are provided with inwardly directed projections 206 and 208, respectively, which extend over the tubes 30 and which are situated at the rear side of the pair of channel means which is illustrated in FIG. 11 so that in this way the tubes 30 are reliably retained in the pair of channel means 202 and 204.

The connecting means 210 of this embodiment is also integral with and forms one piece with the pair of channel means 202 and 204. This connecting means 210 provides also a pair of hinges 212 and 214 by means of which the pair of channel means 202 and 204 are freely turnable with respect to each other for example between the solid line positions illustrated in FIG. 11 and the phantom line position shown therein. The connecting means 210 includes a vertically extending wall portion 216 which extends downwardly from the junction where the hinges 212 and 214 are provided and which carries at its front surface an integral circular wall portion 218 behind which the tubes 30 freely pass as indicated in FIG. 11.

With this embodiment the releasable holding means 220 includes also a channel component 222 which in this case only has a pair of opposed concentric side walls 224 and 226 defining between themselves a hollow interior space for receiving the component 228 of the releasable holding means 220. The component 222 is integrally formed with the channel means 202 while the component 228 is integrally formed with the channel means 204 so that the entire releasable holding means 220 as well as the pair of channel means 202 and 204 and the connecting means 210 therewith form a single, one-piece structure.

The component 228 of the releasable holding means 220 includes a pair of springy plastic fingers 230 and 232 which resiliently tend to move apart from each other beyond the position thereof shown in FIG. 11. These springy fingers 230 and 232 respectively terminate in the enlarged free ends 234 and 236 apparent from FIG. 11. The thickness of the fingers 230 and 232 is somewhat less than the width of the concentric side walls 224 and 226 which are provided at their free edges with inwardly directed lips 238 and 240 which thus extend over the projections 234 and 236 as is clearly apparent from FIGS. 11 and 12. Also, with this embodiment the space at the inner or right end of the component 222 is completely open.

Thus, the free ends of the springy fingers 230 and 232 can easily be received in the hollow interior of the component 222 for sliding along the inner surfaces of the concentric side walls 224 and 226. It will be noted that in this embodiment there is no intermediate wall and it is only the frictional engagement of the projections 234 and 236 with the inner surfaces of the side walls 224 and 226 which maintains the pair of channel means 202 and 204 in their adjusted positions relative to each other. However, the wall 226 is formed adjacent its right end with an opening 238 into which the projection 236 snaps when the parts have the solid line position shown in FIG. 11, so that in this way this embodiment also is provided with a means which limits the movement of the component 228 outwardly of the interior of the component 222. As the pair of channel means 202 and 204 are moved inwardly toward each other toward the phantom line position shown in FIG. 11, for example, the curved configuration of the tooth 236 will enable the latter to move freely out of the opening 238 and slide along the inner surface of the wall 226 while the springy finger 230 will assume the phantom line position shown in FIG. 11, so that in this way the embodiment of FIGS. 11 and 12 provides the frictional engagement at the releasable holding means 220 which will maintain the headset in its adjusted position.

It will be seen that with the above-described embodiments of the invention, the connecting means which interconnects and forms a one-piece structure with the pair of channel means provides a hinged connection between the pair of channel means so that they are freely turnable with respect to each other, while the releasable holding means acts frictionally to releasably hold the pair of channel means in an adjusted position with respect to each other, with the releasable holding means having an infinite number of positions of adjustment. In contrast, with the embodiments of the invention which are described below, the connecting means provides a resilient, springy type of yieldable interconnection between the pair of channel means, while also forming a one-piece structure therewith, and the releasable holding means is capable of releasably holding the pair of channel means in a selected position of adjustment in opposition to the springy force of the connecting means with the releasably holding means in the embodiments described below providing a number of discrete positions of adjustment.

Figure 13:
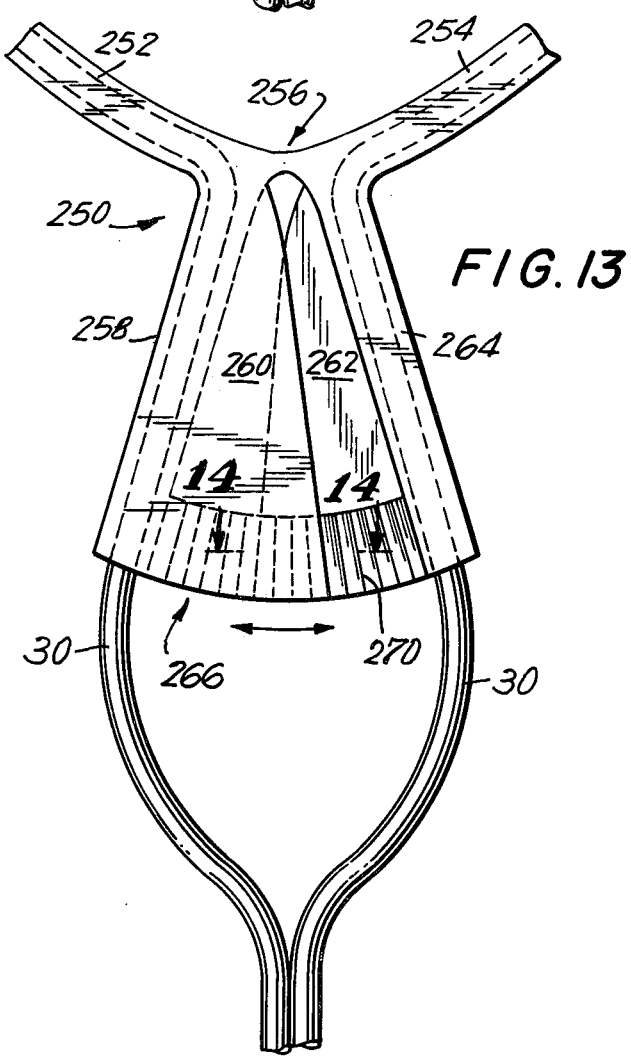
FIG. 13 is a fragmentary elevation of a further embodiment of the invention as seen when looking toward the front thereof with FIG. 13 also showing only the lower end regions of a pair of channel means as well as the details of a connecting means and releasable holding means associated with the pair of channel means.
Figure 14:
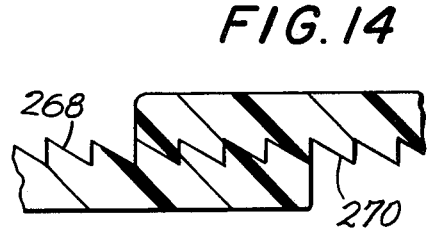
FIG. 14 is a fragmentary sectional plan view taken along line 14—14 of FIG. 13 in the direction of the arrows to illustrate the details of the releasable holding means of the embodiment of FIG. 13.

Thus, referring to FIGS. 13 and 14, the embodiment of the invention illustrated therein includes a headset 250 having a pair of channel means 252 and 254 which receive in their interior the pair of sound tubes 30, respectively. Only the lower end regions of the pair of channel means 252 and 254 are illustrated in FIG. 13. These channel means receive the tubes 30 in the same way as the several different channel means described above, and at their unillustrated portions the channel means 252 and 254 are identical with those of the embodiment of FIGS. 1-5, for example.

It will be seen from FIG. 13 that the lower end regions of the pair of channel means 252 and 254 are substantially L-shaped, each channel means having an elongated substantially straight portion extending from a curved lower end region. At these curved lower end regions of the channel means 252 and 254, there is a connecting means 256 which is integral with the pair of channel means 252 and 254 and which is of a springy plastic material which tends to urge the pair of channel means 252 and 254 toward each other.

The lower straight portion 258 of the channel means 252 is integral with a substantially sector-shaped wall 260 which overlaps a second substantially sector-shaped wall 262 which is integral with the lower straight portion 264 of the channel means 254. Of course it will be understood that the structure is shown in FIG. 3 as it appears when looking toward the front of the headset.

These walls 260 and 262 form part of the releasable holding means 266 which serves to releasably hold the pair of channel means 252 and 254 in an adjusted position with respect to each other. The wall 260 is provided at its lower curved edge region which extends into overlapping relation with the wall 262 with a plurality of teeth 268 extending substantially radially with respect to the lower curved edge of the wall 260. In the same way the wall 262 is formed with a plurality of teeth 270 which extend substantially radially with respect to the lower curved edge of the wall 262. The teeth 270 are directed forwardly, while the teeth 268 are directed rearwardly, and the shape of the teeth, as shown in FIG. 14, is such that these teeth will engage each other to prevent movement of the lower portions 258 and 264 of the pair of channel means apart from each other while the teeth 268 and 270 are in engagement with each other as illustrated in FIG. 14. Thus, the springy connecting means 256 urges the pair of channel means 252 and 254 at their portions which extend upwardly from the connecting means 256 toward each other while urging the straight lower portions 258 and 264 apart from each other. The operator can easily move the portions 258 and 264 toward each other so as to spread the upper parts of the channel means 252 and 254 apart from each other. In this case the teeth 268 and 270 will ride over each other, and when the operator releases the parts 258 and 264, the teeth 268 and 270 will remain in engagement to hold the structure in its adjusted position. In the event that it is desired to bring the ear pieces closer together, the connecting means 256 is of sufficient flexibility to enable the walls 260 and 262 to be displaced apart from each other in a forward and rearward direction so as to easily enable the teeth 268 and 270 to be disengaged from each other, and while these teeth are spaced from each other the operator can turn the lower straight portions 258 and 264 of the pair of channel means apart from each other while the upper portions of the channel means 252 and 254 approach each other, and when the adjusted position is reached the teeth 268 and 270 can again be placed in adjustment with each other to hold the adjusted position. Thus with this embodiment of the invention a springy force at the connecting means 256 is utilized together with the releasable holding means 266 in order to provide the adjusted position for the acoustic head set.

While in the embodiment of FIGS. 13 and 14, the releasable holding means 266 is situated more distant from the upper end regions of the pair of channel means than the connecting means 256, in the embodiment of FIGS. 15 and 16, the releasable holding means is nearer to the upper end regions of the channel means than the connecting means. Thus, referring to FIGS. 15 and 16, it will be seen that this embodiment of the invention includes a pair of channel means 272 and 274 which may be identical with any of the above pairs of channel means and which are shown only at their lower end regions in FIG. 15. The pair of channel means 272 and 274 have open ends beyond which the pair of sound tubes 30 extend in the manner apparent from FIG. 15. Beyond these open ends, the inner side walls of the pair of channel means 272 and 274 have integral extensions 276 and 278 which form part of the connecting means 280. This connecting means 280 includes a ring 282 which is integral with the elongated portions 276 and 278 and which may be closed by a circular plate 284 which may carry any desired indicia, for example. The ring 282 is integral with the elongated plastic portions 276 and 278 which in turn are integral with the inner side walls of the pair of channel means 272 and 274, so that in this embodiment also the connecting means forms a one-piece structure with the pair of channel means. The elongated portions 276 and 278 of the connecting means 280 are springy plastic members which act to urge the pair of channel means 272 and 274 apart from each other toward the dot-dash line position indicated in FIG. 15.

This embodiment of the invention includes a releasable holding means 286 in the form of a front wall 288 of arcuate configuration integral with and projecting to the right from the channel means 272, as viewed in FIG. 15, while behind this front wall 288 the releasable holding means 286 includes a rear wall 290 (FIG. 16) which is integral with and extends to the left from the channel means 274, as viewed in FIG. 15. The rear wall 290 has forwardly directed teeth 292 of the configuration apparent from FIG. 16, with these teeth 292 extending substantially radially with respect to the arcuate wall 290. The wall 288 has at its rear surface teeth 294 which also extend substantially radially with respect to the curved front wall 288. These teeth 294 are adapted to engage the teeth 292 in order to prevent movement of the pair of channel means 272 and 274 apart from each other as a result of the force exerted by the connecting means 280. Thus, when the pair of channel means 272 and 274 are moved toward each other from the dot-dash line position to the solid line position shown in FIG. 15, for example, the teeth 292 and 294 will simply ride over each other and will engage each other to prevent movement of the pair of channel means 272 and 274 apart from each other. However, when it is desired to increase the distance between the pair of ear pieces, then it is a simple matter to deflect the walls 288 and 290 in a forward and rearward direction apart from each other so that the teeth 292 and 294 are disengaged from each other, and at this time it is possible to release the pair of channel means 272 and 274 to be moved apart from each other by the force of the connecting means 280. When the adjusted position is reached the walls 280 and 290 can be released to engage each other at their teeth as illustrated in FIG. 16, and in this way the adjusted position will be retained.

The embodiment of the invention which is illustrated in FIGS. 17-19 includes a pair of elongated channel means 296 and 298 which are respectively identical with the pair of channel means 274 and 272 and which also have their inner side walls integral with a pair of elongated plastic springy extensions 300 and 302 which form part of a connecting means 304. These extensions 300 and 302, however, are connected to a plastic ring 306 in a manner which is somewhat different from the connection of the elongated portions 276 and 278 to the ring 282. Thus it will be seen from FIG. 17 that the springy strip portions 300 and 302 merge into larger plastic portions than in the case of FIG. 15, and these larger plastic portions are situated at diametrically opposed parts of the ring 306. This ring 306 also may be closed by a circular plate 308 which may carry any desired indicia. In this case also the springy force of the connecting means 304 acts to urge the pair of channel means 296 and 298 apart from each other for example from the solid line position to the dot-dash line position indicated in FIG. 17. Of course the structure is shown in FIG. 17 as it appears by looking toward the rear of the structure, whereas the structure is shown in FIG. 15 as it appears from looking toward the front of the structure, and FIG. 13 also shows the structure as it appears from looking toward the front thereof.

The releasable holding means 310 of the embodiment of FIGS. 17-19 includes an elongated curved channel structure 312 made of a plastic material and being integral with the channel means 296. This channel structure 312 has an upper wall 314, a lower wall 316, and a front wall 318 extending between and integral with the upper and lower walls 314 and 316. This front wall 318 is formed with a series of detent apertures 320 which are distributed along the arcuate front wall 318 and which communicate one with the next in the manner apparent from FIGS. 17 and 19. Thus a relatively narrow throat portion 322 is situated between and communicates with each pair of adjacent detent apertures 320.

The releasable holding means 310 further includes an arcuate front wall 324 which is integral with and extends to the left from the channel means 298, as viewed in FIG. 17. A relatively narrow plastic portion 326 is integral with the wall 324 and the channel means 298 so as to afford a pivotal type of connection of the wall 324 to the channel means 298. Thus because of this narrow member 326 it is possible for the wall 324 to tilt with respect to the channel means 298 during movement of the pair of channel means 296 and 298 toward and away from each other.

The wall 324 has an elongated central region of substantially V-shaped cross section, as is apparent from FIG. 18, and a part of the wall 324 is integral with a shank or pin 328 which is thus fixed with the wall 324 and projects from the latter through one of the detent apertures 322. In the interior of the channel structure 312, to the rear of the wall 318, the pin 328 is fixed with a member 330 which prevents axial removal of the pin 328 from the series of detent apertures 320 while at the same time permitting the pin 328 to move from one aperture to the next. This member 330 is in the form of a stud, for example, having a pointed tip which is pushed into the pin 328 with the member 330 remaining fixed with the pin 328, so that the structure will have the condition illustrated in FIG. 18.

The plastic material of the channel 312 is such that it is capable of yielding when the pin 328 is displaced from one detent aperture to the next detent aperture in the manner indicated in FIG. 19. Thus the diameter of the pin 328 is greater than the throat 322 while being almost equal to the diameter of the each aperture 320. Thus the pin 328 can be displaced along the series of detent apertures 320 with the portions of wall 318 above and below the series of detent apartures being capable of yielding as the pin 328 passes through a throat 322, and these walls will snap back as soon as the pin 328 goes beyond a throat 322.

Thus, with this construction when it is desired to adjust the distance of the pair of channel means 296 and 298 with respect to each other, the operator need only move the pair of channel means toward and away from each other, and the pin 328 will progress along the series of detent apertures to be received in a selected one of these apertures when the adjusted position is reached. At the same time, the springy force of the connecting means 304 serves to urge the pair of channel means 296 and 298 apart from each other so that there is no play in the adjusted position. Thus with this embodiment also it is possible for the operator easily and quickly to situate the pair of ear pieces at a desired distance from each other.

It will be noted that with all of the embodiments of the invention described above, there will be no excessive pressure of the ear pieces against the ears of the individual using the acoustic headset of the invention. At the same time the acoustic headset of the invention is made up of the pair of channel means, connecting means, and releasable holding means, all of which in most cases will form a one-piece structure, capable of being quickly and inexpensively molded. Thus, a long trouble-free operating life is assured for any of the above-described embodiments of the invention.

What is claimed is:

1. In an acoustic headset, a pair of elongated channel means for respectively carrying sound tubes which are respectively provided with earpieces respectively situated adjacent upper end regions of said pair of channel means, the latter respectively having lower end regions distant from said upper end regions thereof, connecting means extending between said pair of channel means at said lower end regions thereof and connecting said pair of channel means to each other for movement toward and away from each other for accommodating the distance between said earpieces to the distance between the ears of a given individual, and releasable holding means for releasably holding said pair of channel means for selectively releasably holding said channel means at respective positions defining a range of distances between said earpieces, said pair of channel means, connecting means and releasably holding means forming an integral, continuous, one-piece structure, said releasably holding means including a first holding means component fixed to one of said channel means and projecting toward said other channel means at a point spaced from said connecting means, and a second holding means component fixed to the other of said channel means, said first and second holding means components being formed and positioned for inter-engaging cooperation to selectively retain said pair of channel means at each of a plurality of positions within said range of distances between said earpieces.

2. The combination of claim 1 and wherein said releasable holding means components cooperate frictionally with each other for releasably holding said pair of channel means at a selected distance from each other.

3. The combination of claim 1 and wherein one of said holding means components has a pair of opposed side walls defining between themselves an elongated hollow space and an intermediate wall situated between and spaced from said side walls, while the other of said components includes a pair of fingers received in said space with one of said fingers having an end region frictionally engaging and situated between said intermediate wall and one of said side walls and the other of said components having an end region situated between and frictionally engaging said intermediate wall and the other of said side walls.

4. The combination of claim 1 and wherein one of said components has a pair of opposed side walls defining between themselves a hollow interior space of said one component, and the other of said components including a pair of springy fingers received in said space and pressing against said side walls, respectively, for frictionally holding said pair of channel means at a selected distance from each other.

5. The combination of claim 1 and wherein one of said components has a hollow interior space into which the other of said components extends for frictionally engaging said one component in the interior thereof, and means carried by said one component and cooperating with the other component for limiting the extent to which the latter can be withdrawn from said one component.

6. The combination of claim 1, said pair of components respectively having overlapping surface regions each of which is provided with a series of teeth, and the teeth of one of said surface regions cooperating with the teeth of the other of said surface regions for releasably holding said pair of channel means at a selected distance from each other.

7. The combination of claim 1, one of said components including an elongated arm formed with a series of detent apertures distributed along said arm and communicating one with the next, while the other of said components includes an elongated arm fixedly carrying a detent pin capable of being selectively received in a selected one of said detent apertures while being movable along said one arm from one aperture to the next to provide a selected distance between said pair of channel means.

8. The combination of claim 1 and wherein said connecting means provides a springy, yieldable connection between said pair of channel means and acts on said pair of channel means for yieldably urging the latter to a predetermined position relative to each other.

9. The combination of claim 1 and wherein said connecting means hingedly connects said pair of channel means to each other for free swinging movement relative to each other.

10. The combination of claim 9 and wherein said connecting means includes a central portion situated midway between said pair of channel means and a hinge means connecting each of said channel means to said central portion.

11. The combination of claim 10 and including cap means releasably carried by said central portion for covering the latter.

* * * * *